United States Patent
Yokobayashi et al.

(10) Patent No.: US 9,434,495 B2
(45) Date of Patent: Sep. 6, 2016

(54) SHIELD AND ELECTRON BEAM CONTAINER STERILIZATION EQUIPMENT

(71) Applicant: HITACHI ZOSEN CORPORATION, Osaka (JP)

(72) Inventors: Takayasu Yokobayashi, Osaka (JP); Ichiro Sakai, Osaka (JP)

(73) Assignee: Hitachi Zosen Corporation, Osaka (JP)

( * ) Notice: Subject to any disclaimer, the term of this patent is extended or adjusted under 35 U.S.C. 154(b) by 0 days.

(21) Appl. No.: 14/889,181

(22) PCT Filed: Apr. 25, 2014

(86) PCT No.: PCT/JP2014/061652
§ 371 (c)(1),
(2) Date: Nov. 5, 2015

(87) PCT Pub. No.: WO2014/185251
PCT Pub. Date: Nov. 20, 2014

(65) Prior Publication Data
US 2016/0083131 A1 Mar. 24, 2016

(30) Foreign Application Priority Data
May 13, 2013 (JP) ................... 2013-100818

(51) Int. Cl.
*A61L 2/08* (2006.01)
*B65B 55/08* (2006.01)
(Continued)

(52) U.S. Cl.
CPC ............ *B65B 55/08* (2013.01); *A61L 2/087* (2013.01); *A61L 2/26* (2013.01); *G21K 5/04* (2013.01)

(58) Field of Classification Search
CPC ........ B65B 55/08; A61L 2/087; A61L 2/26; G21K 5/04
See application file for complete search history.

(56) References Cited

U.S. PATENT DOCUMENTS 5,621,780 A * 4/1997 Smith .................. A61N 5/1001
378/119
7,759,661 B2 7/2010 Avnery
(Continued)

FOREIGN PATENT DOCUMENTS

JP 2008-30784 2/2008
JP 2009-526971 7/2009
(Continued)

OTHER PUBLICATIONS

International Search Report in corresponding PCT application PCT/JP2014/061652.
(Continued)

*Primary Examiner* — Wyatt Stoffa
(74) *Attorney, Agent, or Firm* — Fildes & Outland, P.C.

(57) ABSTRACT

Provided is a shield used for container sterilization equipment that inserts, from the mouth of a container (B), an irradiation nozzle (En) having an exit window (Ew) on the distal end of the irradiation nozzle (En) and sterilizes the inner surface of the container (B), the irradiation nozzle (En) being surrounded by composite shields (Wi, Wo). A composite shield block (21) forming the composite shields (Wi, Wo) includes a magnetic shield (24) and an X-ray shield (25) that are disposed in the hollow section of a board-shaped shell (22) made of a corrosion resistant material, and an insulating layer (26) that is interposed between one surface of the board-shaped shell (22) and the magnetic shield (24), between the magnetic shield (24) and the X-ray shield (25), and between the X-ray shield (25) and one surface of the board-shaped shell (22).

6 Claims, 5 Drawing Sheets

(51) Int. Cl.
   *A61L 2/26* (2006.01)
   *G21K 5/04* (2006.01)

(56) References Cited

U.S. PATENT DOCUMENTS

| | | | | |
|---|---|---|---|---|
| 8,021,043 | B2* | 9/2011 | Hawver | G03B 42/02 |
| | | | | 378/189 |
| 8,022,116 | B2* | 9/2011 | Coppens | C08K 3/08 |
| | | | | 523/136 |
| 2005/0098740 | A1 | 5/2005 | Bol et al. | |
| 2008/0073549 | A1* | 3/2008 | Avnery | B65B 55/08 |
| | | | | 250/397 |
| 2012/0279177 | A1 | 11/2012 | Macquet | |
| 2013/0015365 | A1 | 1/2013 | Bufano et al. | |
| 2013/0114796 | A1* | 5/2013 | Funk | G21K 1/025 |
| | | | | 378/149 |
| 2014/0027651 | A1* | 1/2014 | Kawasaki | A61L 2/08 |
| | | | | 250/453.11 |
| 2014/0231673 | A1* | 8/2014 | Yokobayashi | B65B 55/08 |
| | | | | 250/455.11 |
| 2014/0299786 | A1* | 10/2014 | Yokobayashi | B65G 47/847 |
| | | | | 250/455.11 |
| 2015/0287487 | A1* | 10/2015 | Medoff | C10L 5/442 |
| | | | | 250/492.1 |
| 2015/0297765 | A1* | 10/2015 | Krueger | A61L 2/087 |
| | | | | 422/2 |
| 2016/0064111 | A1* | 3/2016 | Sakai | H01J 35/02 |
| | | | | 250/496.1 |

FOREIGN PATENT DOCUMENTS

| | | |
|---|---|---|
| JP | 4859517 | 11/2011 |
| JP | 2012-55556 | 3/2012 |
| WO | 2013/058205 | 4/2013 |

OTHER PUBLICATIONS

English language machine translation of JP 4859517.
English language machine translation of JP 2012-55556.
English language machine translation of JP 2008-30784.

* cited by examiner

SHIELD AND ELECTRON BEAM CONTAINER STERILIZATION EQUIPMENT

TECHNICAL FIELD

The present invention relates to a shield used for an electron beam sterilizer and electron beam container sterilization equipment.

BACKGROUND ART

Electron beams (cathode rays) emitted for sterilizing cellular microorganisms collide with metallic components constituting a sterilizer, for example, a stainless holder for holding a container, and thus the electron beams are attenuated and generate braking X-rays or characteristic X-rays. The X-rays are spread widely and then are reflected and diffracted. For example, X-rays having been collided with a shield three to four times can be attenuated to intensity that does not affect a human body, depending on the intensity of X-rays.

It is known that the direction of an electron beam is curved by the effect of a magnetic field. When the outer surface of a container is sterilized by electron beam irradiation, electron beams are widely emitted to the container from an electron beam generator through a wide exit window. Thus, the influence of geomagnetism does not need to be taken into consideration. In a recent technique, electron beams are passed through the wall surface of a container so as to sterilize the inner surface of the container. An electron dose is kept at a predetermined value or less because an excessive electron dose may cause alteration, coloring, or odor on the container. Thus, the recent technique is applied to only a container having an extremely thin wall surface so as to suppress an electron dose. Moreover, Patent Literature 2 discloses a technique for introducing and emitting electron beams from the mouth of a container. In order to prevent irradiation of electron beams around the mouth of the container, an irradiation blocking plate is provided around the mouth of the container.

For example, in a recent technique proposed in Patent Literature 1, an electron beam irradiation nozzle is inserted into a container from the mouth of the container and then electron beams are emitted to the inner surface of the container from an exit window on the distal end of the irradiation nozzle so as to sterilize the inner surface. In the technique for sterilizing the inner surface with the irradiation nozzle, electron beams emitted from the exit window of the irradiation nozzle are spread but a suppressed electron dose limits a sterilization range, requiring the exit window to move close to the bottom of a container. Thus, the length of the irradiation nozzle needs to be nearly equal to the height of the container. A tall container requires an irradiation nozzle having a length of 30 to 40 cm. Moreover, the irradiation nozzle needs to have an outside diameter so as to be loosely fit into the mouth of the container and requires a cooling structure for cooling heat generated by electron beams. This limits the inside diameter of an electron beam passage to about 10 mm in the irradiation nozzle.

The effect of geomagnetism on the above irradiation nozzle may curve electron beams passing through the electron beam passage and the electron beams are emitted from a biased portion of the exit window, or may collide electron beams with the inner surface of the electron beam passage of the irradiation nozzle before reaching the exit window, resulting in abnormal sterilization.

An experiment has proved that the generation of a magnetic field twice to triple ordinary geomagnetism of about 0.3 (Gauss) may collide electron beams with the inner surface of the irradiation nozzle. Moreover, the direction and intensity of geomagnetism drastically vary depending on solar activities including a magnetic storm, a position on the earth's surface, and a time. Furthermore, the direction and intensity of geomagnetism are considerably affected by a magnetic field parallel to the earth's surface from the north pole to the south pole. The influence of geomagnetism on electron beams is sufficiently greater than that of a magnetic field of a motor for transporting a sterilization equipment container. In the case of rotary type sterilization equipment that sterilizes the inner surface of a container during turning along a circular path, the direction and intensity of geomagnetism are found to greatly vary on the circular path. An experiment has proved that the intensity of geomagnetism is changed by about 1 (Gauss) or more, leading to the possibility of unstable sterilization by electron beams emitted from an irradiation nozzle.

CITATION LIST

Patent Literatures

Patent Literature 1: National Publication of International Patent Application No. 2009-526971
Patent Literature 2: Japanese Patent No. 4859517

SUMMARY OF INVENTION

Technical Problem

However, Patent Literatures 1 and 2 do not describe measures against geomagnetism that affects electron beams passing through an irradiation nozzle.

The present invention is devised to solve the problem. An object of the present invention is to provide a shield and electron beam sterilization equipment that can stably sterilize a container by preventing magnetism from changing an electron beam trajectory.

Solution to Problem

An invention according to a first aspect is a shield used for electron beam container sterilization equipment that sterilizes a container with electron beams emitted to the container, the shield including a composite shield of a magnetic shield layer and an X-ray shield layer between a pair of corrosion resistant layers for protection against a corrosive atmosphere, the magnetic shield layer blocking magnetism while the X-ray shield layer blocks X-rays generated by reflection and diffraction of electron beams, the composite shield including an insulating layer interposed between one of the corrosion resistant layers and the magnetic shield layer, between the magnetic shield layer and the X-ray shield layer, and between the X-ray shield layer and the other corrosion resistant layer.

An invention according to a second aspect is a shield used for electron beam container sterilization equipment that sterilizes a container with electron beams emitted to the container, the shield being composed of a plurality of composite shield blocks, the composite shield block including a magnetic shield and an X-ray shield in the hollow section of a board-shaped shell made of a corrosion resistant material, and an insulating layer between one surface of the board-shaped shell and the magnetic shield, between the magnetic shield and the X-ray shield, and between the X-ray shield and another surface of the board-shaped shell.

An invention according to a third aspect is electron beam container sterilization equipment that inserts, from the mouth of a container, an electron beam irradiation nozzle having an exit window on the distal end of the irradiation nozzle and sterilizes the inner surface of the container, the electron beam irradiation nozzle being surrounded by a shield, the shield being composed of the shield according to one of the first and second aspects.

An invention according to a fourth aspect is electron beam container sterilization equipment that holds containers kept in an upright position, move the containers along a circular path around a vertical pivot axis, moves electron beam irradiation nozzles in synchronization with the containers, moves at least one of the electron beam irradiation nozzle and the container upward or downward, inserts the electron beam irradiation nozzle into the mouth of the container, and sterilizes the inner surface of the container with electron beams emitted from the electron beam irradiation nozzle, the equipment including an inner shield along the inner periphery of the circular path and outer shield along the outer periphery of the circular path, the inner and outer shields each being composed of the shield according to one of the first and second aspects.

Advantageous Effects of Invention

According to the invention of the first aspect, the magnetic shield layer and the X-ray shield layer are disposed between the corrosion resistant layers so as to form a shield layer. Thus, the X-ray shield layer can block and effectively attenuate X-rays. Moreover, the magnetic shield layer can prevent geomagnetism from curving electron beams, allowing the electron beams to stably sterilize the container. Furthermore, the corrosion resistant layers can prevent corrosion in an atmosphere of hydrogen peroxide or ozone, and the insulating layer can prevent galvanic corrosion caused by a potential difference between dissimilar metals.

In this case, "layers" of the shield layer and the corrosion resistant layer include a layer bonded by application, spraying, or vapor deposition on a molded or cut plate or member, and include a shield composed of a magnetic shield layer, an insulating layer, and a corrosion resistant layer with one of the shield layers, for example, the X-ray shield layer serving as a base material.

According to the invention of the second aspect, the magnetic shield and the X-ray shield of the composite shield block are disposed in the hollow section of the board-shaped shell made of a corrosion resistant material. Furthermore, the insulating layer is interposed among the corrosion resistant layer, the magnetic shield, and the X-ray shield. Thus, X-rays can be blocked and effectively attenuated by the X-ray shield and the magnetic shield can prevent geomagnetism from curving electron beams in the electron beam irradiation nozzle, thereby stably sterilizing the inner surface of the container. Moreover, the board-shaped shell can prevent corrosion in a corrosive atmosphere, and the insulating layer can prevent galvanic corrosion caused by a potential difference between dissimilar metals. Furthermore, the magnetic shield and the X-ray shield disposed in the hollow section of the board-shaped shell can facilitate manufacturing and assembly of the composite shield block.

In this case, "shield" indicates only a molded or cut plate or member.

According to the invention of the third aspect, when the electron beam irradiation nozzle is inserted into the container from the mouth to sterilize the inner surface of the container, the shield provided around the electron beam irradiation nozzle can prevent geomagnetism from curving electron beams during the passage of electron beams through the small-diameter electron beam irradiation nozzle. This can stably emit electron beams from the exit window.

According to the invention of the fourth aspect, even if the electron beam irradiation nozzle turning along the circular path considerably changes geomagnetism, the inner and outer shields including composite shields around the circular path can prevent geomagnetism from curving electron beams passing through the electron beam irradiation nozzle, thereby stably sterilizing the inner surface of the container.

DESCRIPTION OF EMBODIMENTS

First Embodiment

Referring to FIGS. 1 to 4, a first embodiment of container sterilization equipment according to the present invention will be described below.

Figure 2:
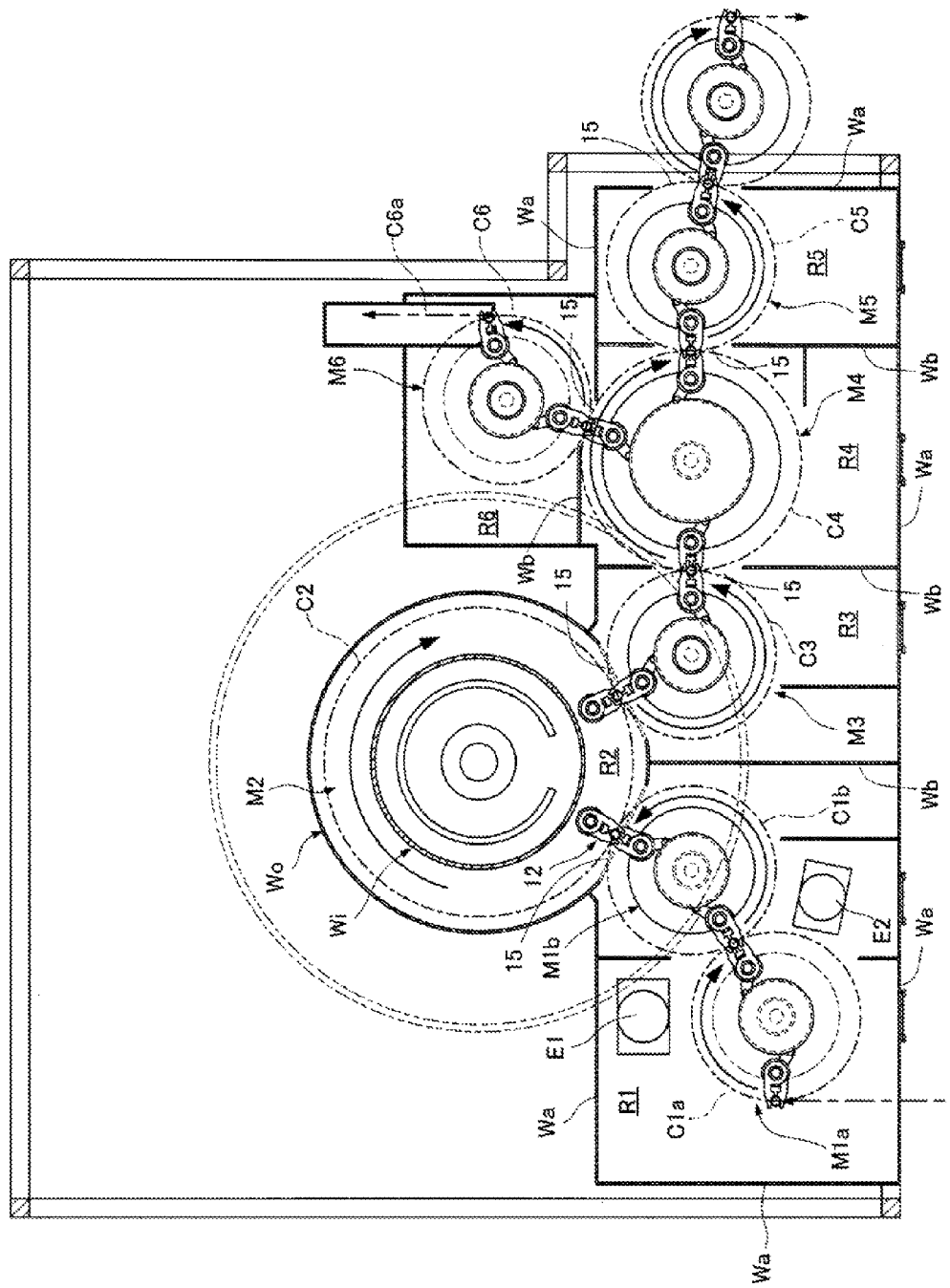
FIG. 2 is a schematic plan view showing a first embodiment of electron beam sterilization equipment including a shield.
Figure 3:
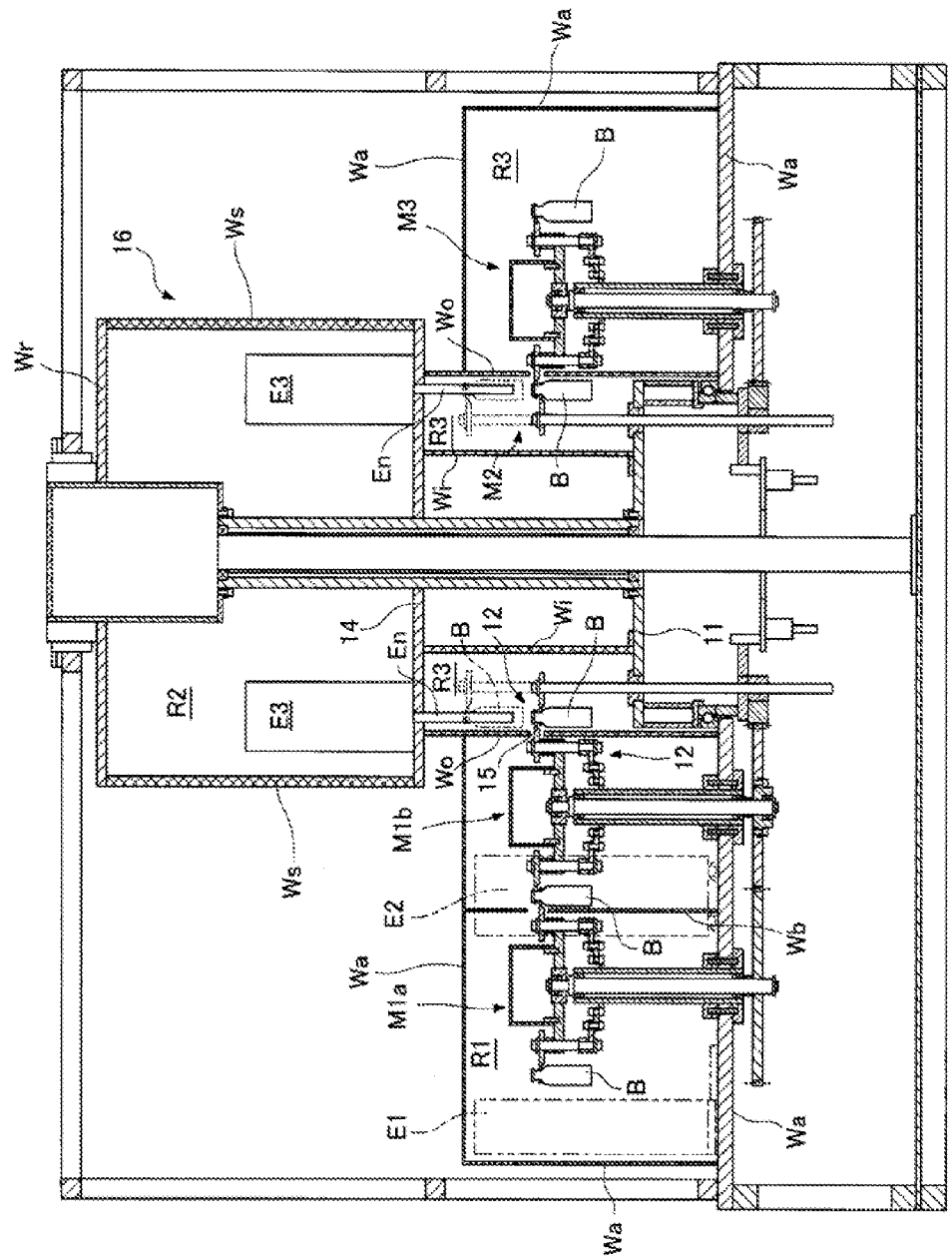
FIG. 3 is a side cross-sectional view showing the electron beam sterilization equipment.
Figure 4:
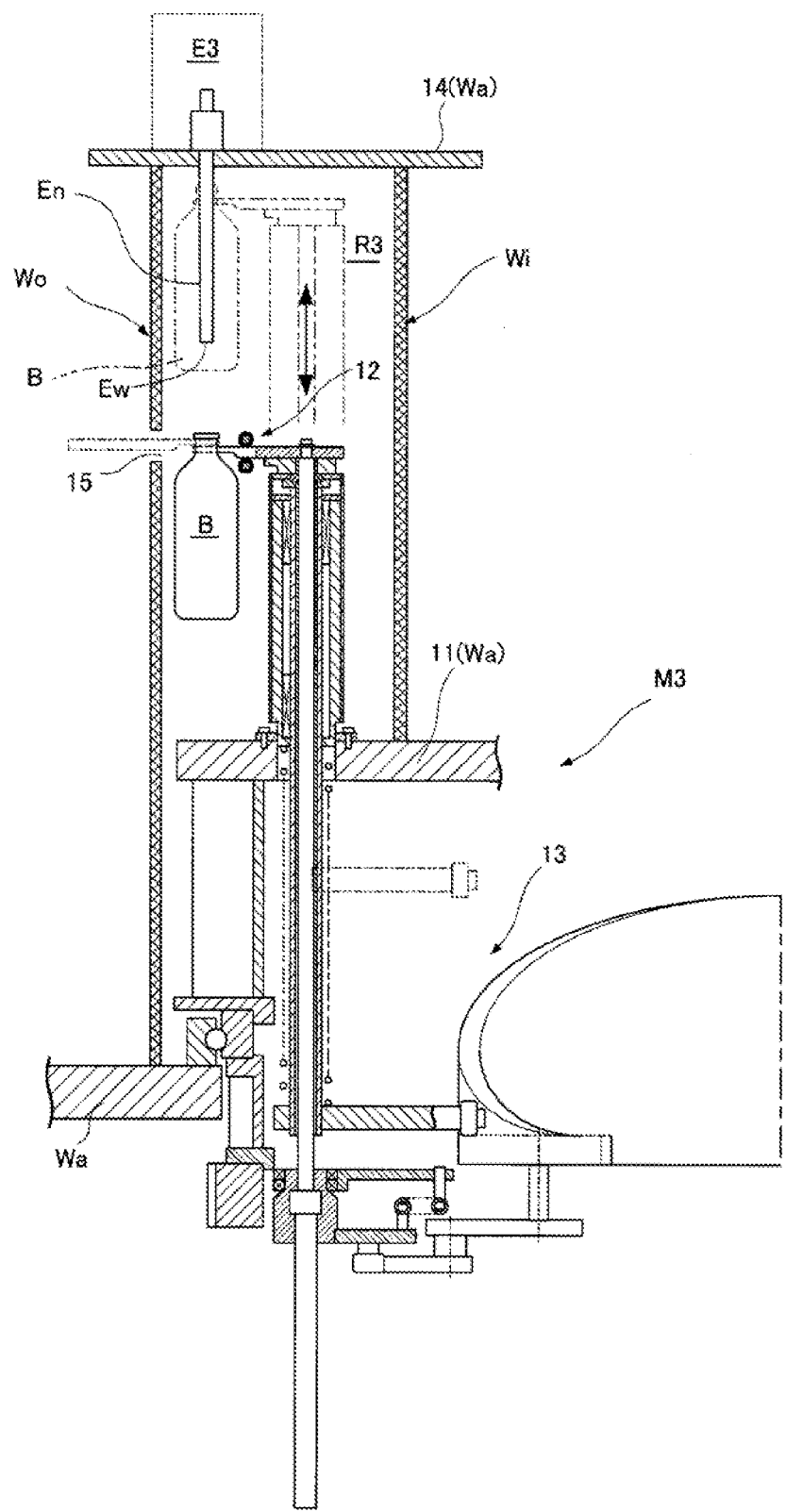
FIG. 4 is a partially enlarged view showing the principal part of an inner sterilizing chamber.

As shown in FIGS. 2 to 4, the container sterilization equipment includes, from the inlet to the outlet of containers B, an outer sterilizing chamber R1, an inner sterilizing chamber R2, a first delivery chamber R3, a second delivery chamber R4, a trap chamber R5, and a reject chamber R6. The chambers R1 to R6 contain rotary conveyors M1a and M1b to M6, respectively, that transport the containers B along circular paths C1a and C1b to C6 around vertical axes. The circular paths C1a and C1b to C5 are connected in series. The circular path C6 of the reject chamber R6 is branched and connected to the circular path C4 of the second delivery chamber R4. If the container B is insufficiently sterilized and is transported to the circular path C6, the container B is discharged from a delivery path C6a.

In the outer sterilizing chamber R1, the two rotary conveyors M1a and M1b are disposed in series to sequentially transport the containers B, which are held by neck holders 12, along the circular paths C1a and C1b. Outside the circular path C1a near the inlet, a first electron beam irradiator E1 is installed to sterilize substantially a half of the circumference of the container B. Outside the circular path C1b near the outlet, a second electron beam irradiator E2 is installed to sterilize substantially the other half of the circumference of the container B.

In the inner sterilizing chamber R2, the neck holders 12 with elevating mechanisms 13 are installed at regular intervals on the outer periphery of a turning table 11 of the rotary conveyor M2. The neck holders 12 move up and down the containers B in a predetermined range with the cam elevating mechanisms 13 while transporting the containers B along the circular path C2. On a ceiling turning plate 14 above the turning table 11, third electron beam irradiators E3 are installed for the respective neck holders 12. The third electron beam irradiator E3 includes a suspended irradiation nozzle (electron beam irradiation nozzle) En that emits electron beams from an exit window Ew on the lower end (distal end) of the nozzle. The irradiation nozzle En is inserted from the mouth of the container B that is lifted by the elevating mechanism 13 while being moved along the circular path C2. Subsequently, electron beams emitted from the exit window Ew sterilize the inner surface of the container B.

The elevating mechanism 13 that moves up and down the container B may move the irradiation nozzle En instead. Alternatively, both of the container B and the irradiation nozzle En may be moved up and down.

In the first delivery chamber R3, the second delivery chamber R4, and the trap chamber R5, the containers B sequentially discharged from the inner sterilizing chamber R2 are moved along the circular paths C3 to C5 by the rotary conveyors M3 and M5; meanwhile, the insufficiently sterilized container B is discharged to the reject chamber R6.

The floor surfaces, the ceiling surfaces, and the outer surfaces of the chambers R1 to R6 are surrounded by main shield walls Wa for blocking X-rays that are generated by reflecting and diffracting electron beams to peripheral members after the electron beams are emitted from the first to third electron beam irradiators E1 to E3. Moreover, the chambers R1 to R6 are partitioned with partition shield walls Wb for blocking X-rays. The partition shield wall Wb has a transport opening 15 formed for delivering the container B. In the chambers R1 to R6, electrons react with oxygen in the air to generate ozone during sterilization. Sterilization for killing bacteria with hydrogen peroxide or peracetic acid is conducted in the chambers R1 to R6 periodically, for example, once a week. Thus, the chambers R1 to R6 are placed into a corrosive atmosphere containing a large amount of hydrogen peroxide or ozone. For this reason, the main shield wall Wa and the partition shield wall Wb are X-ray shields covered with cover members made of corrosion resistant metals. For example, the X-ray shield is a lead plate covered with, for example, a stainless metallic plate having high resistance to corrosion.

In the inner sterilizing chamber R2, the partition shield wall Wb is assembled to the turning table 11 and the ceiling turning plate 14. Of the main shield walls Wa and the partition shield walls Wb, an inner composite shield Wi circular in plan view is raised along the inner side of the circular path C2 and an outer composite shield Wo is raised along the outer side of the circular path C2, from the turning table 11 to the ceiling turning plate 14. The inner and outer composite shields Wi and Wo each include an X-ray shield layer, a magnetic shield layer, and a high-corrosion resisting layer. As a matter of course, the composite shield may be assembled to the turning table 11 and the ceiling turning plate 14.

Moreover, an irradiator shield chamber 16 is formed above the ceiling turning plate 14. The irradiator shield chamber 16 includes an outer wall shield We covering the outer periphery of the third electron beam irradiator E3 and a top plate shield Wr covering the top of the irradiator shield chamber 16. The outer wall shield We includes a composite shield block of an X-ray shield layer, a magnetic shield layer, and a high-corrosion resisting layer. The top plate shield Wr includes a shield that is formed by covering an X-ray shield with a cover member made of a corrosion resistant metal.

Figure 1A:
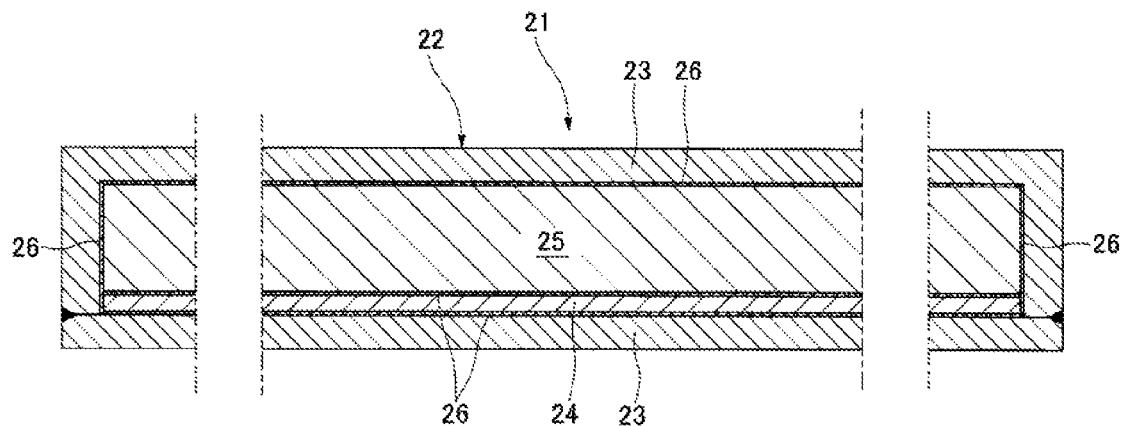
FIGS. 1A and 1B are a partially enlarged cross-sectional view and an exploded perspective view of an embodiment of a composite shield block that forms a composite shield according to the present invention.
Figure 1B:
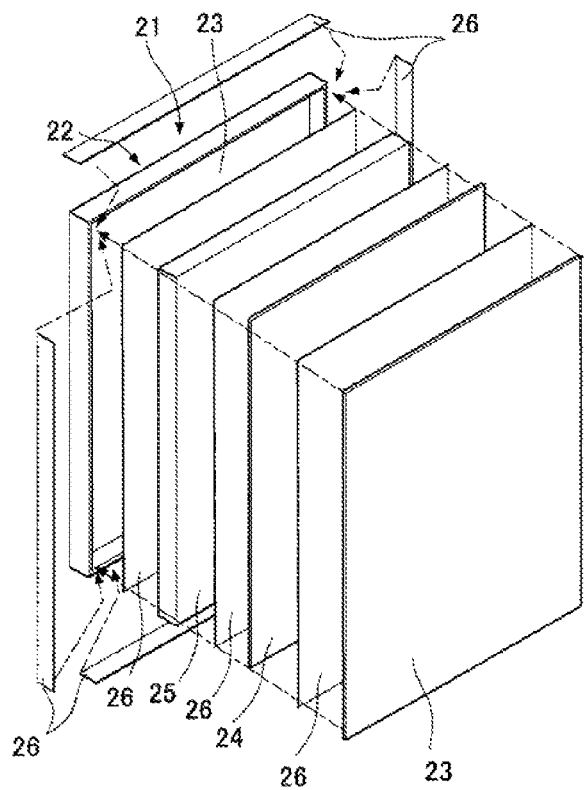

Specifically, as shown in FIG. 1, a composite shield block 21 forming the inner and outer composite shields Wi and Wo is a combination of a magnetic shield 24 forming a magnetic shield layer and an X-ray shield 25 forming an X-ray shield layer between corrosion resistant plates (corrosion resistant layers) 23 forming a pair of high-corrosion resisting layers with an insulating layer 26 interposed between the magnetic shield 24 and the X-ray shield 25.

For example, the corrosion resistant plates 23 made of stainless steel (nonmetallic materials can be used) form a hollow board-shaped shell (a box having an open surface) 22. The plate-like magnetic shield 24 and the X-ray shield 25 composed of, for example, a lead plate are fit into the hollow section of the board-shaped shell 22. The magnetic shield 24 is made of, for example, highly permeable magnetic metals such as high permeable Mu-Metal (containing a permalloy and Mo, Mn, Cu, and Cr, e.g., 78Ni-5Mo-4Cu—Fe or 36Ni—Fe) and an iron-nickel alloy (52Ni—Fe). The insulating layer 26 made of, for example, insulating adhesives such as epoxy resin and silicon resin is provided between the corrosion resistant plate 23 and the magnetic shield 24, between the magnetic shield 24 and the X-ray shield 25, and between the X-ray shield 25 and the corrosion resistant plate 23. The insulating layer 26 is provided to prevent galvanic corrosion caused by a potential difference between dissimilar metals. As a matter of course, the insulating layer 26 is also provided on the upper and lower sides of the hollow section as well as the right and left sides of the hollow section. The insulating layer 26 is a coating of an insulating adhesive or a bonded adhesive sheet made of an insulating adhesive.

In the composite shield block 21, preferably, the corrosion resistant plate 23 made of stainless steel is 0.5 to 2.5 mm in thickness, the Mu-Metal magnetic shield 24 is 0.3 to 3 mm in thickness, and the lead X-ray shield 25 is 2 to 15 mm in thickness depending on the intensity of X-rays. The composite shield block 21 is so large and heavy as to be handled by an operator and has the property of being easily bent. For example, the composite shield block 21 preferably has a thickness of 4 to 20 mm.

The board-shaped shell 22 is shaped like a box having an open surface (a shielded surface in FIG. 1). The board-shaped shell 22 may be shaped like a box having open right and left sides and/or open upper and lower sides.

The magnetic shield 24 illustrated like a plate in FIG. 1 may be shaped like a strip or a mesh as long as shielding against geomagnetism can be obtained.

The board-shaped shell 22 is used in the embodiment. The composite shield block 21 may include a magnetic shield layer, an insulating layer, and a corrosion resistant layer that are formed by application, spraying, or vapor deposition on the X-ray shield 25 serving as a base material.

According to the first embodiment, the magnetic shield 24 and the X-ray shield 25 are disposed between the corrosion resistant plates 23 in the hollow section of the board-shaped shell 22, forming the composite shield block 21. Thus, the X-ray shield 25 can shield the composite shield block 21 from X-rays so as to effectively attenuate the X-rays, and the magnetic shield 24 can prevent geomagnetism from curving electron beams in the electron beam irradiation nozzle En, thereby stably sterilizing the inner surface of the container B. The corrosion resistant plate 23 can prevent corrosion in an atmosphere of hydrogen peroxide or ozone, and the insulating layer 26 can prevent galvanic corrosion caused by a potential difference between dissimilar metals. Moreover, the magnetic shield 24 and the X-ray shield 25 are disposed in the hollow section of the board-shaped shell 22 so as to form the composite shield block 21, facilitating the manufacturing and assembly of the composite shield block 21.

Furthermore, in the inner sterilizing chamber R2, even if the electron beam irradiation nozzle En turning along the circular path C2 considerably changes the influence of geomagnetism, the magnetic shield 24 contained in the composite shield block 21 forming the inner and outer composite shields Wi and Wo can prevent geomagnetism from curving electron beams in the electron beam irradiation nozzle En, thereby stably sterilizing the inner surface of the container B.

Moreover, a composite shield is used for the outer wall shield We disposed on the outer periphery of the third electron beam irradiator E3 in the irradiator shield chamber 16. This can stably generate electron beams from the third electron beam irradiator E3 without being affected by a change of geomagnetism or an environmental magnetic field.

Second Embodiment

Figure 5:
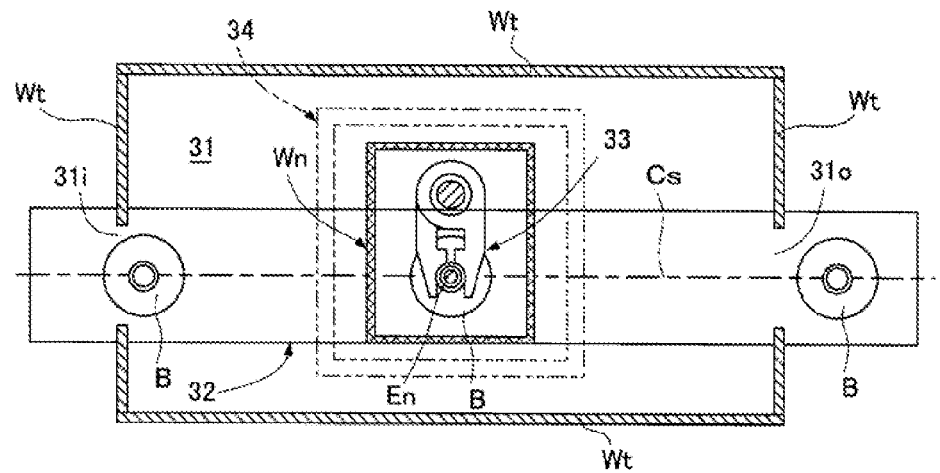
FIG. 5 is a schematic plan cross-sectional view showing an inner sterilizing part in electron beam sterilization equipment including a shield according to a second embodiment.
Figure 6:
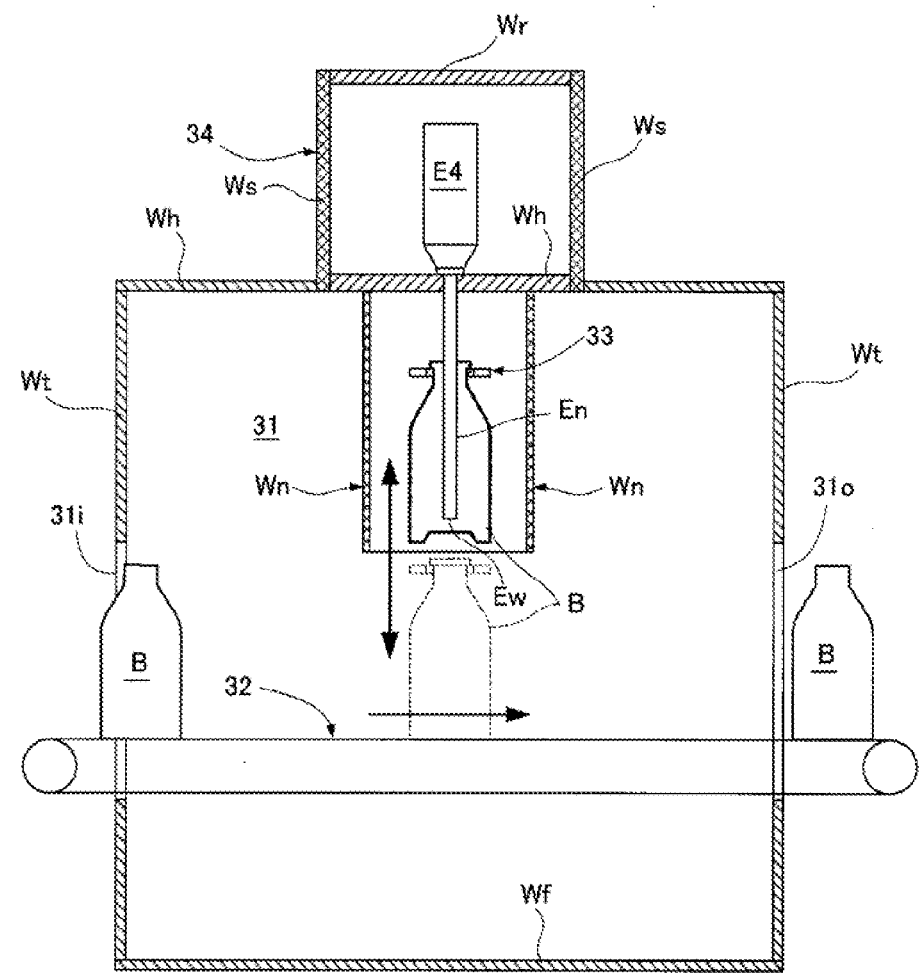
FIG. 6 is a schematic side cross-sectional view showing the inner sterilizing part in the electron beam sterilization equipment.

FIGS. 5 and 6 show a second embodiment of electron beam sterilization equipment according to the present invention. FIGS. 5 and 6 are schematic plan and side cross-sectional views of an inner sterilizing part. The same members as those of the first embodiment are indicated by the same reference numerals and the explanation thereof is omitted.

A belt conveyor 32, an example of a container conveyor, is installed in an inner sterilizing chamber 31 surrounded by a side wall shield Wt, a bottom wall shield Wf, and a ceiling wall shield Wh, the belt conveyor 32 extending along a container transport path Cs from a container inlet 31*i* to a container outlet 31*o* of the inner sterilizing chamber 31. The belt conveyor 32 transports containers B that are intermittently moved at regular intervals. The inner sterilizing chamber 31 corresponding to a container stop position on the belt conveyor 32 is provided with a container elevating device (not shown) that holds the neck of the container B with a pair of neck holding arms 33 and then lifts the container B to a predetermined height. The inner sterilizing chamber 31 includes the side wall shield Wt, the bottom wall shield Wf, and the ceiling wall shield Wh that block X-rays generated by reflection and diffraction of electron beams. The X-ray shields are covered with cover members made of corrosion resistant metals.

On the ceiling wall shield Wh, a fourth electron beam irradiator E4 is installed to sterilize the inner surface of the container B. An irradiation nozzle (electron beam irradiation nozzle) En having an exit window Ew on the distal end (lower end) of the nozzle is suspended from the fourth electron beam irradiator E4 through the ceiling wall shield Wh. The irradiation nozzle En is inserted from the mouth of the container B that is lifted by the container elevating device via the neck holding arms 33, and then the inner surface of the container B is sterilized by electron beams emitted from the exit window Bw.

A nozzle shield (composite shield) Wn is installed on the outer periphery of the irradiation nozzle En and is suspended from the ceiling wall shield Wh. Moreover, an irradiator shield chamber 34 surrounding the fourth electron beam irradiator E4 is formed on the ceiling wall shield Wh. The irradiator shield chamber 34 includes outer wall shields (composite shield) We and a top plate shield Wr. The outer wall shield We includes a composite shield of an X-ray shield layer, a magnetic shield layer, and a corrosion resistant layer. The top plate shield Wr includes a shield that is formed by covering an X-ray shield with a cover member made of a corrosion resistant metal.

According to the second embodiment, the nozzle shield Wn including a composite shield is installed on the outer periphery of the irradiation nozzle En. Thus, electron beams passing through the irradiation nozzle En can be linearly emitted stably from the exit window Ew without being affected by an environmental magnetic field or geomagnetism, thereby stably sterilizing the inner surface of the container B.

Furthermore, the outer wall shield We installed on the outer periphery of the fourth electron beam irradiator E4 in the irradiator shield chamber 34 is a composite shield. Thus, electron beams can be stably generated from the fourth electron beam irradiator E4 without being affected by a change of geomagnetism or an environmental magnetic field.

The invention claimed is:

1. A shield used for electron beam container sterilization equipment that sterilizes a container with electron beams emitted to the container,
   the shield including a composite shield of a magnetic shield layer and an X-ray shield layer between a pair of corrosion resistant layers for protection against a corrosive atmosphere, the magnetic shield layer blocking magnetism while the X-ray shield layer blocks X-rays generated by reflection and diffraction of electron beams,
   the composite shield including an insulating layer interposed between one of the corrosion resistant layers and the magnetic shield layer, between the magnetic shield layer and the X-ray shield layer, and between the X-ray shield layer and the other corrosion resistant layer.

2. Electron beam container sterilization equipment that inserts, from a mouth of a container, an electron beam irradiation nozzle having an exit window on a distal end of the irradiation nozzle and sterilizes an inner surface of the container,
   the electron beam irradiation nozzle being surrounded by a shield,
   the shield being composed of the shield according to claim 1.

3. Electron beam container sterilization equipment that holds containers kept in an upright position, move the containers along a circular path around a vertical pivot axis, moves electron beam irradiation nozzles in synchronization with the containers, moves at least one of the electron beam irradiation nozzle and the container upward or downward, inserts the electron beam irradiation nozzle into a mouth of the container, and sterilizes an inner surface of the container with electron beams emitted front the electron beam irradiation nozzle,
   the equipment including an inner shield along an inner periphery of the circular path and an outer shield along an outer periphery of the circular path,
   the inner and outer shields each being composed of the shield according to claim 1.

4. A shield used for electron beam container sterilization equipment that sterilizes a container with electron beams emitted to the container, the shield being composed of a plurality of composite shield blocks, the composite shield block including a magnetic shield and an X-ray shield in a hollow section of a board-shaped shell made of a corrosion resistant material, and an insulating layer between one surface of the board-shaped shell and the magnetic shield, between the magnetic shield and the X-ray shield, and between the X-ray shield and another surface of the board-shaped shell;

the magnetic shield blocking magnetism while the X-ray shield blocks X-rays generated by reflection and diffraction of electron beams.

5. Electron beam container sterilization equipment that inserts, from a mouth of a container, an electron beam irradiation nozzle having an exit window on a distal end of the irradiation nozzle and sterilizes an inner surface of the container, the electron beam irradiation nozzle being surrounded by a shield, the shield being composed of the shield according to claim 4.

6. Electron beam container sterilization equipment that holds containers kept in an upright position, move the containers along a circular path around a vertical pivot axis, moves electron beam irradiation nozzles in synchronization with the containers, moves at least one of the electron beam irradiation nozzle and the container upward or downward, inserts the electron beam irradiation nozzle into a mouth of the container, and sterilizes an inner surface of the container with electron beams emitted from the electron beam irradiation nozzle, the equipment including an inner shield along an inner periphery of the circular path and an outer shield along an outer periphery of the circular path, the inner and outer shields each being composed of the shield according to claim 4.

* * * * *